United States Patent [19]

Gaenzler et al.

[11] 4,069,381

[45] Jan. 17, 1978

[54] METHOD FOR PREPARING GLYCOL ESTERS

[75] Inventors: Wolfgang Gaenzler, Darmstadt-Eberstadt; Klaus Kabs, Seeheim; Günter Schroeder, Ober-Ramstadt, all of Germany

[73] Assignee: Rohm GmbH, Darmstadt, Germany

[21] Appl. No.: 415,453

[22] Filed: Nov. 12, 1973

[30] Foreign Application Priority Data

Nov. 20, 1972 Germany .............................. 2256847

[51] Int. Cl.² .............................................. C07C 67/05
[52] U.S. Cl. ........................................ 560/1; 560/198; 560/224; 560/246
[58] Field of Search ........... 260/497 R, 468 R, 485 G, 260/486 R

[56] References Cited

U.S. PATENT DOCUMENTS

| 2,702,232 | 2/1955 | Arnold et al. | 260/497 R |
|---|---|---|---|
| 3,299,110 | 1/1967 | Pine | 260/497 R |
| 3,335,174 | 8/1967 | Norton | 260/497 R |
| 3,689,535 | 9/1972 | Kollar | 260/497 R |

OTHER PUBLICATIONS

Shimizu, CA. vol. 76, 139, 950.

*Primary Examiner*—Anton H. Sutto
*Assistant Examiner*—Michael Shippen
*Attorney, Agent, or Firm*—Curtis, Morris & Safford

[57] ABSTRACT

An improved method for making glycol monoesters and diesters of carboxylic acid by the reaction of an olefin and oxygen in the presence of a carboxylic acid and a catalyst, wherein said catalyst includes a compound of a metal of groups IVB – VIIB having an atomic number between 40 and 42 inclusive or between 72 and 75 inclusive, i.e. zirconium, niobium, molybdenum, hafnium, tantalum, tungsten, or rhenium.

11 Claims, No Drawings

METHOD FOR PREPARING GLYCOL ESTERS

The present invention relates to a process for the preparation of glycol esters by the oxidation of an olefin with oxygen and a carboxylic acid in the presence of a catalyst.

It is known in the art to react olefins with molecular oxygen in a carboxylic acid to form the corresponding glycol monoester or diester in the presence of a catalyst. In particular, the use of specific catalysts is the subject of a number of patents.

French patent No. 1,421,288 teaches the use of a bromide, optionally with the simultaneous use of a metal salt, as an oxidation catalyst. The reaction takes place in a mixture of an aromatic hydrocarbon and a carboxylic acid.

According to British patent 1,124,862 the formation of glycol esters is favored by the reaction of an olefin with a nitrate or nitrite in a carboxylic acid using a palladium salt as a catalyst.

According to French patent 1,419,966, noble metals of Group VIII of the Periodic Table are good catalysts for the oxidation of olefins in, for example, acetic acid. As oxidizing agents in this process, nitric acid, or the acids set free by this acid, are employed.

According to U.S. Pat. No. 3,542,857 olefins and molecular oxygen are used in a carboxylic acid to form glycolic acid esters if a cerium salt soluble in the carboxylic acid is employed as a catalyst.

In German patent publication 1,931,563, iodine or iodide ion together with a cation which is an alkali metal cation, a nitrogenous cation, or a cation of a heavy metal having a periodic number from 21 to 30 or 48 is taught as a favorable catalyst for glycol ester formation from an olefin and oxygen in the simultaneous presence of a carboxylic acid.

The same process is, according to German patent publication 1,948,787, favorably influenced by catalyst systems comprising bromine or chlorine or a bromine- or chlorine-containing compound on the one hand and, on the other hand, containing a cation of a multivalent metal selected from the group consisting of tellurium, cerium, arsenic, antimony, manganese, or cobalt.

Also, according to German patent publication 2,126,505 multivalent metal cations, namely tellurium, cerium, antimony, manganese, vanadium, gallium, arsenic, cobalt, copper, selenium, chromium, and silver, in combination with bromine or chlorine or hydrobromic or hydrochloric acid are effective catalysts for the preparation of glycol esters from olefins, oxygen, and a carboxylic acid.

Finally, British patent 1,058,995 should be mentioned. This patent teaches catalysts favoring the same process and which comprise a palladium-II-salt, an acetate of an alkali metal or alkaline earth metal, of copper, iron, tin, or nickel, and a halide of the metals just mentioned.

The selectivity of the known catalysts and/or the yields achieved by their use are not completely satisfactory. Further, in any catalyst system employing a platinum metal, it is necessary to recover the noble metal from the used catalyst system and to rework it.

It has now been found that certain metal compounds permit the reaction of an olefin with oxygen in a carboxylic acid, or in an inert medium containing a carboxylic acid, with high selectivity and outstanding yields. According to the present invention, the catalysts consist essentially of at least one compound of zirconium, niobium, molybdenum, hafnium, tantalum, tungsten, or rhenium. The process can be carried out discontinuously or continuously and oxygen can be used per se or, to the extent that the presence of a relatively large content of inert gas can be tolerated, in the form of air.

Further, from the position in the Periodic Table of the metals to be used in the form of their compounds, it can be predicted that technetium, which joins zirconium, niobium, and molybdenum in the second transition group, would also have a catalytic effect. However, no practical experience has been had with compounds of this metal.

The catalysts of the invention are compounds of seven metals which belong to the second and third transition groups of the Periodic Table. Compounds of the metals of the corresponding first transition group, namely titanium, vanadium, chromium, and manganese, have already been proposed in German patent publication 1,931,563 as catalysts for the oxidation of olefins. That the heavier homologs of these previously proposed metals, i.e. those which lie at the heart of the present invention, have not yet been investigated for their catalytic efficacy can be explained by the following consideration, well known to one skilled in the art, namely that in general, within a particular group, although the elements of the second and third transition groups possess properties similar to one another, they nevertheless are clearly different from their lighter homologs [cf. Cotton and Wilkinson, "Anorganische Chemie," page 849 (1968)].

The metal compounds to be used according to the present invention, which metal compounds can be used alone or in mixtures with each other, are advantageously employed in the form of their halides. The halide ion which increases the catalytic effect, can also be introduced in the form of the soluble halide of another non-catalytic cation, e.g. a metal halide, ammonium halide, or as a free hydrohalic acid, provided that the aforementioned catalytic metals are present in the form of a compound soluble in the reaction medium, for example as their acetates. It should be mentioned that special corrosion problems arise particularly in the use of hydrochloric acid, for example.

The catalytic efficacy of the compounds of zirconium, niobium, molybdenum, hafnium, tantalum, tungsten, or rhenium, can be increased by the simultaneous use of a compound of the metals lithium, sodium, potassium, titanium, vanadium, chromium, manganese, iron, cobalt, nickel, copper, zinc, aluminum, or silver. Catalyst systems which comprise cations of the metals zirconium, niobium, molybdenum, hafnium, tantalum, tungsten, and rhenium, halide anions, and also compounds of the metals lithium, sodium, potassium, titanium, vanadium, chromium, manganese, iron, cobalt, nickel, copper, zinc, aluminum, or silver, permit the formation of glycol esters with particularly good yields and high selectivity.

When catalysts and co-catalysts of this kind are used jointly, they suitably are present such that the mol ratio of the metals therein is between 1:10 and 10:1, preferably between 1:3 and 3:1.

Like the aforementioned processes, known to those skilled in the art, the process of the present invention also takes place at elevated temperatures, advantageously in a range between 50° and 200° C. However, one can operate at temperatures below or above the aforementioned temperature region if one accepts, on the one hand, a lower reaction velocity or, on the other hand, greater expenditures for equipment.

It is evident that for the achievement of satisfactory conversions or yields, the reaction according to the present invention advantageously proceeds under pressure. In a discontinuous performance of the new process, the minimum pressure to be employed is largely determined by the amount of the olefin to be introduced into the reaction medium under pressure, by the oxygen which is to be added, and as well by the reaction temperature which is to be used. In a continuous performance of the process, it has proved advantageous to permit glycol ester formation to take place in a pressure region between 10 atmospheres and 75 atmospheres. If one operates below or above this pressure region, the same observations made above for the choice of temperature are also basically valid.

The amount in which the compounds or mixtures of compounds employed as catalysts are used in the present invention can vary between wide limits. For example, the mol ratio of the catalytically active compounds to the olefin to be oxidized may be from 1:100 to 1:100,000. The life of the catalyst which plays a particularly important role in the economy of a continuous performance of the process, depends to a large extent on the degree of purity of the starting materials.

If the aforementioned elements are not added in the form of a halide, but hydrogen halides, or the halides of other, different, non-catalytic cations are employed, it is advantageous to adjust the amount of halogen so that at least one halogen atom is present for each two atoms of Zr, Nb, Mo, Hf, Ta, W, or Re. In the catalyst used in Example 1 hereinafter, which has shown a particularly good efficacy, this requirement is verified.

Among the catalysts which can be employed according to the invention, those comprising a halogen-containing tantalum-V-compound and an aluminum compound, for example aluminum acetate, have proved to be particularly advantageous.

Among the olefins to be used in practicing the present invention, ethylene and propylene have heretofore had a preferred position from the point of view of the commercial significance of the products which are formed. However, in principle, the higher olefins can be converted to the corresponding glycol esters in an analogous fashion.

The carboxylic acid which is employed and which is a reactant can be any monocarboxylic acid or dicarboxylic acid which is resistant to oxidation and which is liquid at the reaction temperature. Advantageously the acid is also liquid at lower temperatures of about 40° C. Examples of such acids are acetic acid, propionic acid, butyric acid, pivalic acid, methacrylic acid, cyclohexene-3-carboxylic acid-1 and heptadecane dicarboxylic acid-1,8 or -1,9.

Although the use, as a reaction medium, of a carboxylic acid which takes part in the ester formation represents the most preferred embodiment of the method of the present invention, in special cases an inert solvent, for example benzene, toluene, or xylene, can advantageously also be present. Even the glycol esters formed as the end product can be viewed as such an inert solvent.

The glycol esters which can be prepared according to the invention find wide uses as solvents and plasticizers, as is well known. The glycol esters of higher carboxylic acids play an important role in the surface-active agent industry. Since the hydrolysis of glycol esters is well known to be a simple and smoothly-running reaction, the process of the present invention is also suitable for the preparation of glycols. The hydrolytically removed acid, optionally after concentration, can be returned to the process for ester formation.

A better understanding of the present invention and of its many advantages will be had by referring to the following specific examples given by way of illustration.

In each of the examples below, the following technique was used.

In a heatable two-liter autoclave coated with "Teflon," the reaction medium, comprising acetic acid as a solvent and acetic acid anhydride as a water-binding agent, was introduced together with the catalyst mixture. Then the autoclave was closed and the olefin was then introduced into the autoclave under pressure.

When propylene was used, it was introduced under pressure in several steps, because of its low liquefaction pressure of about 10 atmospheres, in order to achieve saturation of the reaction medium. Thereafter, oxygen or compressed air was added and the autoclave was heated to about 140° C.

The contents of the autoclave were worked up by distillation. The reaction products formed were analyzed by gas chromatography and NMR-spectroscopy according to known techniques.

EXAMPLE 1

1 g of tantalum-V-chloride is boiled in 450 ml of glacial acetic acid to form $Ta_2O_3Cl(OOCCH_3)_3$ with release of hydrochloric acid [cf. Chem. Ber. 62, 1688 (1929)]. The mol ratio of metal to halogen in this compound is 1:0.5. 50 ml of acetic acid anhydride and 2 grams of aluminum acetate are added to this solution. After saturation with propylene and the further introduction of about 10 atmospheres of this gas, 20 atmospheres of oxygen were added and the mixture was heated to 136° C.

Distillative working up gave:
43.4 g of propylene glycol diacetate;
1 g of propylene glycol monoacetate; and
traces of propylene glycol.

EXAMPLE 2

1 g of tungsten hexachloride and 2 g of aluminum acetate were dissolved in 600 ml of glacial acetic acid and 60 ml of acetic acid anhydride. Then 10 atmospheres of propylene and 20 atmospheres of oxygen were introduced under pressure and the autoclave contents were heated to 130° C. After cooling, the reaction mixture was worked up by distillation.

The following materials were found:
11.1 g of propylene glycol diacetate;
0.98 g of propylene glycol monoacetate; and
traces of propylene glycol.

EXAMPLE 3

2.5 g of zirconium-IV-chloride were boiled in 100 ml of glacial acetic acid for 2.5 hours. This forms zirconium-IV-acetate with the release of hydrochloric acid. [cf. Chem. Ber. 40, 810 (1907)]. The mixture was then filtered. 600 ml of acetic acid and 80 ml of acetic acid anhydride are added, together with 2 g of copper-II-acetate and 5 g of potassium bromide, and the solution is saturated with propylene. After the further introduction under pressure of about 10 atmospheres of propylene, 20 atmospheres of oxygen are added. The reaction took place at 130° – 140° C.

Working up produced 21 g of propylene glycol diacetate.

EXAMPLE 4

1 g of tantalum-V-chloride was dissolved in 400 ml of glacial acetic acid and 50 ml of acetic acid anhydride. After saturation with propylene and the further introduction under pressure of about 10 atmospheres of propylene, 20 atmospheres of oxygen were additionally added and the mixture was heated to about 140° C. After cooling, the batch was distilled. 20 g of propylene glycol diacetate were formed.

EXAMPLE 5

0.7 g of rhenium-V-chloride and 3 g of aluminum acetate were dissolved in 475 ml of glacial acetic acid and 25 ml of acetic acid anhydride. This solution was saturated with propylene and an additional 10 atmospheres of propylene were introduced. After introducing 80 atmospheres of compressed air, the mixture was heated to 140° C. and held at this temperature for about 2 hours. After cooling, the batch was distillatively worked up.

The yield was:
20.2 g of glycol diacetate;
1.2 g of glycol monoacetate; and
0.5 g of glycol.

EXAMPLE 6

3 g of acetylacetone are introduced into 25 ml of glacial acetic acid. 4.1 g of molybdenum-V-chloride are dissolved in this solution. 1.9 g of titanium-IV-chloride are added with stirring at room temperature. After stirring for 30 minutes, the crystals are removed by vacuum filtration. The crystalline compound formed in this manner (2.7 g — apparently triacetylacetonato-titanium-IV-hexachloromolybdate) are dissolved in 450 ml of acetic acid and 50 ml of acetic acid anhydride.

After saturation of this solution with propylene, an additional 10 atmospheres of propylene are added and, subsequently, 20 atmospheres of oxygen. After heating at 150° C., the product is worked up by distillation.

The following were found:
38.05 g of glycol diacetate;
2.0 g of glycol monoacetate; and
0.96 g of glycol.

EXAMPLE 7

A solution of 2 g of molybdenum-V-chloride in 450 ml of glacial acetic acid and 50 ml of acetic acid anhydride is saturated with propylene. Then, 20 atmospheres of oxygen are introduced under pressure and the mixture is heated to 150° C. Working up the reaction product by distillation gave 5.6 g of propylene glycol diacetate.

EXAMPLE 8

2 g of ReCl$_5$, 1 g of gallium trichloride, and 1 g of lithium chloride were dissolved in 720 ml of glacial acetic acid and 80 ml of acetic acid anhydride. After saturation with propylene, 20 atmospheres of oxygen were introduced under pressure and the mixture heated to 150° C. Distillation of the reaction solution gave 8.9 g of propylene glycol diacetate and 1 g of the monoacetate.

EXAMPLE 9

A polynuclear niobium-titanium-complex is prepared, along the lines of Example 6, from 4.05 g of niobium-V-chloride, 2 g of acetylacetone and 1.1 ml of titanium-IV-chloride. The complex is dissolved in 640 ml of glacial acetic acid and 10 ml of acetic acid anhydride. The mixture is then treated as in the previous Examples. 4 g of propylene glycol diacetate are obtained.

EXAMPLE 10

A polynuclear complex is prepared from rhenium-V-chloride, titanium-IV-chloride, and acetylacetone in a manner like that prescribed by Dilthey, Chem. Ber. 37, 589 (1904). The complex is dissolved in 500 ml of glacial acetic acid and 50 ml of acetic acid anhydride. Further processing is as in the previous Examples. 8.3 g of propylene glycol diacetate are obtained.

EXAMPLE 11

2 g of molybdenum-V-chloride and 2 g of manganese-III-acetate are dissolved in 450 ml of glacial acetic acid and 50 ml of acetic acid anhydride and then combined with propylene and oxygen as in the earlier Examples. The material is then heated to 150° C. After cooling and distillation, 37.8 g of propylene glycol diacetate are obtained.

EXAMPLE 12

1.5 g of rhenium-V-chloride and 3 g CuCl$_2$ are dissolved in 60 ml of glacial acetic acid and 50 ml of acetic acid anhydride. Thereafter the mixture is handled as in the earlier Examples. On working up, 17.7 g of propylene glycol diacetate and 1 g of propylene glycol monoacetate are obtained.

EXAMPLE 13

0.5 g of rhenium-V-chloride, 1 g copper-II-chloride and 1 g iron-III-chloride are dissolved in 500 ml of glacial acetic acid and 50 ml of acetic acid anhydride and then treated as in the earlier Examples. On working up, 20.2 g of propylene glycol diacetate are obtained.

EXAMPLE 14

2 g of niobium-V-chloride and 2 g of copper-II-chloride, after solution in 500 ml of glacial acetic acid and 50 ml of acetic acid anhydride, are combined with oxygen and propylene as in the earlier Examples and heated to 150° C. Working up of the reaction solution gave 26.3 g of propylene glycol diacetate.

EXAMPLE 15

1 g of tantalum-V-chloride and 2 g of copper-II-chloride are dissolved in 500 ml of glacial acetic acid and 50 ml of acetic acid anhydride. Thereafter, the material is treated as in the earlier Examples. 19.3 g of propylene glycol diacetate and 1.2 g of propylene glycol monoacetate are obtained.

What is claimed is:

1. In a method for making glycol monoesters and glycol diesters of a carboxylic acid by reacting an olefin with oxygen in a reaction medium comprising or consisting essentially of a carboxylic acid in the presence of a catalyst, the improvement wherein said reaction is performed at an elevated pressure, above atmospheric pressure, and wherein said catalyst consists essentially of (A) a compound, soluble in said reaction medium, of a catalytic metal of Groups IVB – VIIB of the Periodic Table having an atomic number between 40 and 42 inclusive or between 72 and 75 inclusive or consists essentially of (B) a catalyst as defined in (A) in combination with the compound, soluble in said reaction medium, of a further metal selected from the group consisting of lithium, sodium, potassium, titanium, vanadium, chromium, manganese, iron, cobalt, nickel, copper, zinc, aluminum, or silver.

2. A method as in claim 1 wherein said compound of said catalytic metal is a halide.

3. A method as in claim 1 wherein said compound of said further metal is a halide.

4. A method as in claim 1 wherein halide ions are additionally present in said reaction medium.

5. A method as in claim 1 wherein said catalyst is as defined in (A).

6. A method as in claim 1 wherein said catalyst is as defined in (B).

7. A method as in claim 1 wherein said catalyst is a combination of a tantalum-V-compound and an aluminum compound.

8. A method as in claim 1 wherein said reaction is performed at an elevated temperature, above room temperature.

9. A method as in claim 1 wherein said reaction is performed at a temperature between about 50° C. and about 200° C.

10. A method as in claim 1 wherein said reaction is performed at a pressure between about 10 atmospheres and about 75 atmospheres.

11. A method as in claim 1 wherein said reaction medium comprises halide ions in an amount such that at least one halide ion is present for each two atoms of the catalytic metal present.

* * * * *